United States Patent [19]

Halloran et al.

[11] Patent Number: 5,300,285
[45] Date of Patent: Apr. 5, 1994

[54] PERMANENT WAVING WITH SILICONES

[75] Inventors: Daniel J. Halloran, Midland, Mich.; Gail J. Dehli, Louisville, Ky.

[73] Assignee: Dow Corning Corporation, Midland, Mich.

[21] Appl. No.: 959,828

[22] Filed: Oct. 13, 1992

[51] Int. Cl.⁵ .................... A61K 7/09; A45D 7/04
[52] U.S. Cl. ........................... 424/71; 132/204
[58] Field of Search ........... 424/71, 70, 72; 528/10; 132/204

[56] References Cited

U.S. PATENT DOCUMENTS

| | | | |
|---|---|---|---|
| 3,987,127 | 10/1976 | Dickie | 522/107 |
| 4,401,500 | 8/1983 | Hamada | 524/588 |
| 4,551,634 | 5/1984 | Hatanaka | 522/99 |
| 4,558,147 | 12/1985 | Eckberg | 522/99 |
| 4,560,554 | 12/1985 | Kubo | 424/71 |
| 4,585,669 | 4/1986 | Eckberg | 528/15 |
| 4,798,722 | 1/1989 | Edman | 424/72 |
| 5,002,762 | 3/1991 | Bolich | 424/71 |
| 5,032,460 | 7/1991 | Kantner | 528/12 |
| 5,045,310 | 9/1991 | Halloran | 424/71 |
| 5,049,377 | 9/1991 | Lamb | 424/70 |

*Primary Examiner*—Thurman K. Page
*Assistant Examiner*—Sally Gardner
*Attorney, Agent, or Firm*—James L. DeCesare

[57] ABSTRACT

A process for permanent waving of hair by a reaction in which cystine bridges are reduced to cysteine, the hair reshaped, and the reaction reversed. The improvement in the process resides in the step of reversing the reaction by applying to hair a composition which includes a vinyl functional silicone, a solvent, and a free radical photoinitiator. The free radical photoinitiator is a compound which undergoes intramolecular photocleavage and contains the acetophenone chromophore, such as dimethoxyphenylacetophenone; diethoxyacetophenone; hydroxydimethylacetophenone; 1-benzoylcyclohexanol; 1-phenyl-1,2-propanedione-2-O-benzoyl oxime; and 2-hydroxy-2-methyl-1-phenylpropan-1-one. Both cyclic and linear vinyl functional silicones can be employed. Permanent hair waving neutralizer compositions are also described.

1 Claim, No Drawings

PERMANENT WAVING WITH SILICONES

BACKGROUND OF THE INVENTION

This invention is directed to a method of waving hair and to a silicone based neutralizer composition useful in the permanent waving of hair.

Keratin is a fibrous protein composed of eighteen different kinds of amino acids. It is widely distributed in hair and constitutes the major component thereof. Keratin is characterized by a crosslinked structure having one disulfide bond (—S—S—) per average ten to twenty amino acid residues. It is most frequently represented as cystine which has the formula $HO_2CC(NH_2)HCH_2S-SCH_2C(NH_2)HCO_2H$.

The first basic step in a permanent waving process is the partial reduction of cystine $HO_2CC(NH_2)HCH_2S-SCH_2C(NH_2)HCO_2H$ to cysteine $HO_2CC(NH_2)HCH_2SH$. Typically, a waving lotion containing thioglycolic acid is used in this step, in a reaction in which cystine bridges are reduced to cysteine. After the hair has been reshaped, this reaction is reversed by the application to the hair of a neutralizer, which is a solution containing an oxidant such as hydrogen peroxide. Cysteine residues formed during the reduction step are converted back into cystine upon neutralization.

While hydrogen peroxide is environmentally safe and physiologically harmless, it suffers from the disadvantages that (i) special stabilizers are required to assure stability; (ii) complexing agents are needed to bind up metallic impurities which may have a catalytic effect; and (iii) hair can be lightened at certain concentrations and pH values.

Thus, a need exists in the art for alternative forms of permanent wave neutralizer compositions. The present invention provides such an alternative in the form of a silicone based composition which has been found to effectively function as a keratin crosslinking agent in the permanent waving of human hair.

It is believed that the silicone becomes part of a covalent crosslink between hair keratin fibers in providing a wave. In addition, use of the silicone has the advantage that the silicone imparts to the hair added benefits such as conditioning of the hair as well providing softness of feel.

SUMMARY OF THE INVENTION

The invention relates to a hair waving process and to a composition for use in the process. More particularly, a silicone base neutralizer is employed to reform cystine-like structure from cysteine residues produced during the reduction phase of the permanent waving process. The neutralizer composition of the present invention includes a vinyl functional silicone, a free radical photoinitiator, and a solvent.

As a substitute for hydrogen peroxide based neutralizer solutions, the composition of the present invention possesses the advantage of simultaneously functioning as a keratin crosslinking agent, while at the same time imparting to the hair benefits such as conditioning and softness of feel.

These and other objects, features, and advantages, of the present invention should become more apparent from a consideration of the following detailed description thereof.

DETAILED DESCRIPTION OF THE INVENTION

The neutralizer composition includes as essential ingredients a vinyl functional silicone, a free radical photoinitiator, and a solvent. The composition may additionally contain wetting and foaming agents to improve spreading and retention of the composition on the hair, as well as other conditioning agents to enhance a smooth texture, improve ease of combing, and to increase control of fly-away.

Both cyclic and linear vinyl functional silicones may be used. Suitable vinyl functional silicones comprehended as being within the scope of the invention are compounds which can be represented by the following formulas:

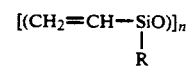

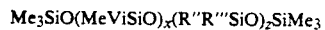

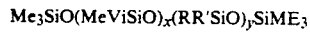

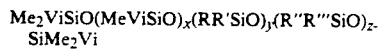

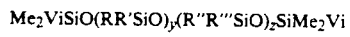

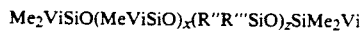

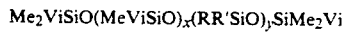

In the above formulas, n is an integer having a value of three to about thirty. Preferably n is five. R, R', R", and R'", each represent an alkyl group of one to six carbon atoms or phenyl. Preferably R, R', R", and R'" are each methyl. Me is methyl. Vi is $CH_2=CH-$. The integers x, y, and z, each have a value of one to about one thousand. The first formula set forth above represents a cyclic vinyl functional silicone, while the remainder of the formulas are representations of linear materials. As compounds, such vinyl functional silicones are known in the art, as are the methods for their preparation. These silicone compounds are all commercially available.

The concept of the crosslinking of human hair with a vinyl functional silicone is believed to take place in accordance with the mechanism shown below, in which a cyclic vinyl functional silicone is used for purposes of illustration. In the following scenario, K represents $HO_2CC(NH_2)HCH_2-$.

$$n\ KSH + (CH_2=CH-\underset{R}{\overset{|}{Si}}O)_n + \text{Photo Initiator} \xrightarrow[\text{Room Temp.}]{\text{UV Light}}$$

$$(K-S-CH_2CH_2-\underset{R}{\overset{|}{Si}}O)_n$$

(reduced Keratin)

(Keratin Crosslink)

The free radical photoinitiator must be a compound capable of generating radicals by the absorption of optical energy. Ultraviolet light sensitive photoinitiators or blends of such photoinitiators which are employed must be capable of initiating the above reaction under wavelengths preferably within the range of 350-385 nm.

In the process according to the present invention, hair is soaked in a solution containing the vinyl functional silicone, the photoinitiator, and a solvent, for one to five minutes. The treated hair is then placed under an ultraviolet light for a period of about fifteen minutes to affect the photocure induced crosslink.

Among the various free radical photoinitiators suitable for purposes of the present invention are dimethoxyphenylacetophenone known as DMPA, which is sold under the trademark IRGACURE® 651 by Ciba-Geigy Corporation, Plastics & Additives Division, Hawthorne, N.Y. There may also be employed compounds such as diethoxyacetophenone known as DEAP; hydroxydimethylacetophenone; 1-benzoylcyclohexanol; and 1-phenyl-1,2-propanedione-2-O-benzoyl oxime. The compound most preferred in accordance with the present invention is 2-hydroxy-2-methyl-1-phenylpropan-1-one, sold under the trademark DAROCUR® 1173 by EM Industries, Hawthorne, N.Y. These free radical photoinitiators are of a category of compounds which undergo intramolecular photocleavage, and possess the acetophenone chromophore.

As a solvent, there may be used alcohols, hydrocarbons, halogenated hydrocarbons, or volatile silicones. Representative solvents are ethanol, isopropyl alcohol, mineral spirits, trichlorethane, and dichlorotetrafluoroethane.

Where it is desired to use a silicone solvent, the volatile silicone in accordance with the present invention is a low viscosity methylsilicone fluid. The methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{\frac{1}{2}}$, $(CH_3)_2SiO_{2/2}$, $(CH_3)SiO_{3/2}$, and $SiO_{4/2}$. These units are present in such molar amounts such that there is an average of from about two to three methyl groups per silicon atom in the methylsilicone fluid, and the fluid has a viscosity of less than about one hundred centistokes measured at twenty-five degrees Centigrade.

The methylsilicone fluid contains dimethylsiloxane units and optionally trimethylsiloxane units. Preferably, the methylsilicone fluid has a viscosity of less than about ten centistokes such as cyclopolysiloxanes of the general formula $[(CH_3)_2SiO]_x$, and linear siloxanes of the general formula $(CH_3)_3SiO[(CH_3)_2SiO]_ySi(CH_3)_3$, in which x is an integer having a value of from three to ten, and y is an integer having a value of from zero to about four.

Such volatile silicones have boiling points generally less than about two hundred-fifty degrees Centigrade, and viscosities preferably generally less than about ten centistokes measured at twenty-five degrees Centigrade, most preferably 0.65 to 5.0 centistokes. The cyclopolysiloxanes have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $(Me_2SiO)_3$; octamethylcyclotetrasiloxane which has a boiling point of 171 degrees Centigrade and the formula $(Me_2SiO)_4$; and decamethylcyclopentasiloxane which has a boiling point of 205 degrees Centigrade and the formula $(Me_2SiO)_5$.

These methylsilicone fluids may be used alone, or as mixtures in combinations of two or more. Mixtures of the methylsilicone fluids will result in a volatile material having an evaporating behavior different from any one of the individual methylsilicone fluids. The methylsilicone fluids and their methods of preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxy; haloalkyl groups; aralkyl groups; and acrylate; for example.

The composition of the present invention is suitable for use in permanent waving processes which may be characterized as hot wave processes, mild wave processes, and cold wave processes. In a typical cold wave process for example, the hair is first shampooed, and the freshly shampooed and still damp hair is divided into about forty to sixty tresses. Each tress is wetted with the waving lotion and wound onto plastic curlers. The size of the curler determines the nature of the resultant wave. Small curlers for example result in tighter waves. The hair is rinsed thoroughly, and neutralized with the neutralizer solution. The hair is then unwound, rinsed again, and either dried or set into a desired style.

In the method according to the present invention, curled reduced hair is treated with the silicone based neutralizer composition for one to five minutes, followed by exposure of the hair to a UV lamp at room temperature for about fifteen minutes. The treatment has been found to impart a permanent wave to the hair which is indistinguishable with respect to curl tightness, from hair treated with hydrogen peroxide based neutralizer solutions.

The following example is set forth for the purpose of further illustrating the concepts embodied in the present invention.

EXAMPLE I

A tress of hair was treated with thioglycolic acid reducing agent and rinsed to a neutral pH. To the curled hair was applied for one minute a solution containing five grams of a cyclic vinyl functional silicone having the formula $[(CH_2=CHRSiO)]_n$ in which R was methyl and n was three. The solution in addition contained one gram of the free radical photoinitiator compound 2-hydroxy-2-methyl-1-phenylpropan-1-one sold under the trademark DAROCUR ® 1173 by EM Industries, Hawthorne, N.Y.; and ninety-four grams of ethanol solvent. To each tress was applied 0.1–2.0 grams of solution. The treated hair tress was placed under an ultraviolet lamp for fifteen minutes. A tight curl was observed and the curl was not distinguishable from a hydrogen peroxide control used for comparative purposes. It was also observed that the hair had a conditioned effect as well as a softer feel relative to the hydrogen peroxide control. The observations were subjective evaluations.

Neutralizer compositions according to the present invention preferably contain 0.5–20 percent by weight of the vinyl functional silicone, 0.1–1.0 percent by weight of the free radical photoinitiator, with the balance of the composition being the solvent and other optional additives.

The compositions of this invention may contain a surfactant selected from the group consisting of anionic and amphoteric surfactants. The surfactant system should provide an acceptable level of foam on the hair and may comprise one or more water soluble detergents, i.e., an anionic or amphoteric surfactant. Suitable anionic detergents include sulfonated and sulfated alkyl, aralkyl and alkaryl anionic detergents; alkyl succinates; alkyl sulfosuccinates and N-alkyl sarcosinates. Especially preferred are the sodium, magnesium, ammonium, and the mono-, di- and triethanolamine salts of alkyl and aralkyl sulfates as well as the salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include, among others, sodium lauryl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500. Particularly preferred amphoteric surfactants are the substituted quaternary hydroxy cycloimidinic acid alkali metal alcoholates described in U.S. Pat. No. 2,528,378.

The most preferred of the amphoteric surfactants are the substituted quaternary hydroxy cycloimidinic acid alkali metal alkoxymethyl carboxylates described in U.S. Pat. No. 2,781,354. The betaines may have the structure:

$$R^1R^2R^3N^+(CH_2)_mCOO^-$$

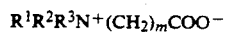

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

$$R^1R^2R^3N^+(CH_2)_mSO_3^-$$

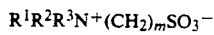

wherein $R^1$, $R^2$, $R^3$, and m are defined as above. Specific useful sultaines are for example 3-(dodecyldimethylammonio)-propane-1-sulfonate, and 3-(tetradecyldimethylammonio)ethane-1-sulfonate.

The compositions of this invention may contain a nonionic surfactant. The nonionic surfactants of the present invention are selected from the group consisting of fatty acid alkanolamide and amine oxide surfactants. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms.

For purposes of this invention the alkanolamide and amine oxide surfactants are preferred. In general, the fatty acid diethanolamides and N-alkyl dimethylamine oxides are preferred for use in the compositions. Especially preferred are the fatty acid diethanolamides and n-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

Additional categories of surfactant materials may also be included such as cationic and zwitterionic surfactants, and representative compounds are set forth in detail in U.S. Pat. No. 4,902,499, issued Feb. 20, 1990, which is considered to be incorporated herein by reference.

Other adjuvants may be added to the compositions of this invention such as thickeners, perfumes, colorants, electrolytes, pH control ingredients, foam boosters and foam stabilizers, antimicrobials, antioxidants, ultraviolet light absorbers and medicaments. For example, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps or more preferably in the range of 1000 to 4000 cps as measured at 25° C. are usually suitable.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as sodium or ammonium chloride, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention.

The perfumes which can be used in the compositions are the cosmetically acceptable perfumes. Colorants are used to confer a color to the composition and may generally be used. Although not required, it is preferred to employ an acid to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid.

If for special purposes conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl) piperazine or of piperazine-bis-acrylamide and piperazine, poly-(dimethylbutenylammonium chloride)-$\alpha,\omega$-bis-(triethanolammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of conditioners may also be employed.

A preservative may be required and representative preservatives which may be employed include about 0.1–0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

Other variations and modifications may be made in the compounds, compositions, and methods described herein without departing from the essential features and concepts of the present invention. The forms of the invention described herein are exemplary only and are not intended as limitations on the scope of the invention as defined in the appended claims.

That which is claimed is:

1. In a process for permanent waving of hair by a reaction in which cystine bridges are reduced to cysteine, the hair reshaped, and the reaction reversed, the improvement comprising reversing the reaction by applying to hair a composition comprising (i) a vinyl functional silicone; (ii) a solvent selected from the group consisting of ethanol, isopropyl alcohol, mineral spirits, trichloroethane, dichloroethane, hexamethyldisiloxane, octamethylcyclotetrasiloxane, and decamethylcyclopentasiloxane; and (iii) a free radical photoinitiator selected from the group consisting of dimethoxyphenylacetophenone, diethoxyacetophenone, hydroxydimethylacetophenone, 1-benzoylcyclohexanol, 1-phenyl-1,2-propanedione-2-O-benzoyl oxime, and 2-hydroxy-2-methyl-1-phenylpropan-1-one; the vinyl functional silicone having the formula:

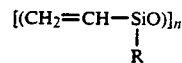

wherein n is an integer having a value of three to about thirty, and R is an alkyl group of one to six carbon atoms or phenyl.